US006551258B1

(12) United States Patent
Herling et al.

(10) Patent No.: US 6,551,258 B1
(45) Date of Patent: Apr. 22, 2003

(54) METHODS AND APPARATUS FOR JOINT LAXITY MEASUREMENTS

(75) Inventors: Derald E. Herling, Corvallis, OR (US); Paul A. Borsa, Ypsilanti, MI (US); Eric L. Sauers, Phoenix, AZ (US)

(73) Assignee: The State of Oregon Acting by and through the State Board of Higher Education on Behalf of Oregon State Univerisity, Corvallis, OR (US)

( * ) Notice: Subject to any disclaimer, the term of this patent is extended or adjusted under 35 U.S.C. 154(b) by 38 days.

(21) Appl. No.: 09/631,213

(22) Filed: Aug. 2, 2000

(51) Int. Cl.[7] ............................................... A61B 5/103
(52) U.S. Cl. .................................................. 600/595
(58) Field of Search ...................... 600/587, 595

(56) References Cited

U.S. PATENT DOCUMENTS

| | | |
|---|---|---|
| 4,485,825 A | 12/1984 | Domján et al. |
| 4,571,834 A | 2/1986 | Fraser et al. |
| 4,583,554 A | 4/1986 | Mittelman et al. |
| 4,583,555 A | 4/1986 | Malcom et al. |
| 4,799,497 A | 1/1989 | RIley, II |
| 4,800,897 A | 1/1989 | Nilsson |
| 4,804,000 A | 2/1989 | Lamb et al. |
| 4,909,262 A | 3/1990 | Halpern et al. |
| 5,014,719 A | 5/1991 | McLeod |
| 5,156,163 A | 10/1992 | Watkins et al. |
| 5,228,454 A | 7/1993 | Siegler |
| 5,335,674 A | 8/1994 | Siegler |
| 5,586,559 A | 12/1996 | Stone et al. |
| 5,628,722 A | * 5/1997 | Solomonow et al. ......... 602/26 |
| 5,961,474 A | 10/1999 | Reis |
| 6,042,555 A | 3/2000 | Kramer et al. |

OTHER PUBLICATIONS

Veeger, H. E. J. et al., "Parameters for Modeling the Upper Extremity", *J. Biomechanics* 30:647–652 (1997).
Ciullo, Jerome Vincent, *Shoulder Injuries in Sport*, pp. 7–36 (1996).
Johnson, G.R., Anderson, J.M., "Measurement of Three–Dimensional Shoulder Movement by an Electromagnetic Sensor," *Clinical Biomechanics* 5:131–136 (1990).

* cited by examiner

*Primary Examiner*—Max F. Hindenburg
*Assistant Examiner*—Pamela L Wingood
(74) *Attorney, Agent, or Firm*—Klarquist Sparkman, LLP

(57) ABSTRACT

An instrumented arthrometer includes displacement sensors configured to be attached to joint-reference locations. An applied force produces a joint displacement that is indicated by the displacement sensors. A force sensor measures the force applied to produce a corresponding displacement, and force/displacement data are stored on a hard disk or other computer-readable medium. A controller displays displacement/force data with comparison data based on a displacement/force data for the same joint prior to therapy or with a normal range of joint displacement/force data. In a specific example, the displacement sensors are electromagnetic sensors that measure displacement in three dimensions, and stiffness/displacement data is displayed in three dimensions.

7 Claims, 8 Drawing Sheets

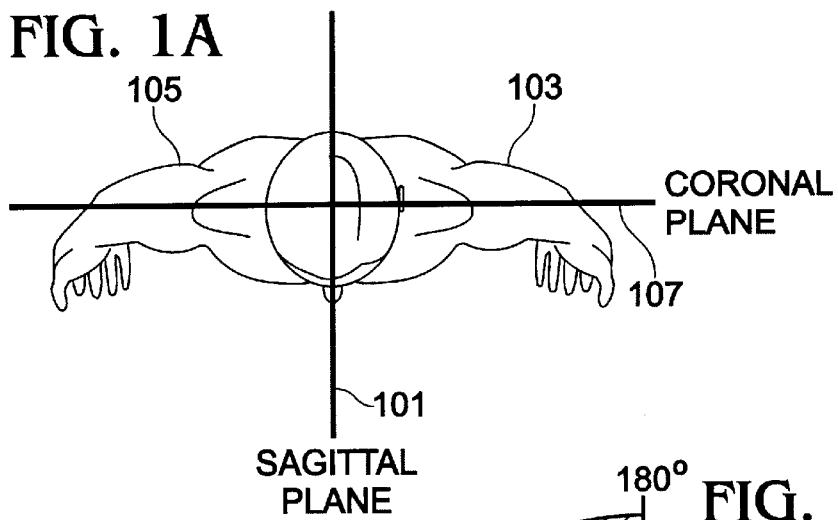
FIG. 1A
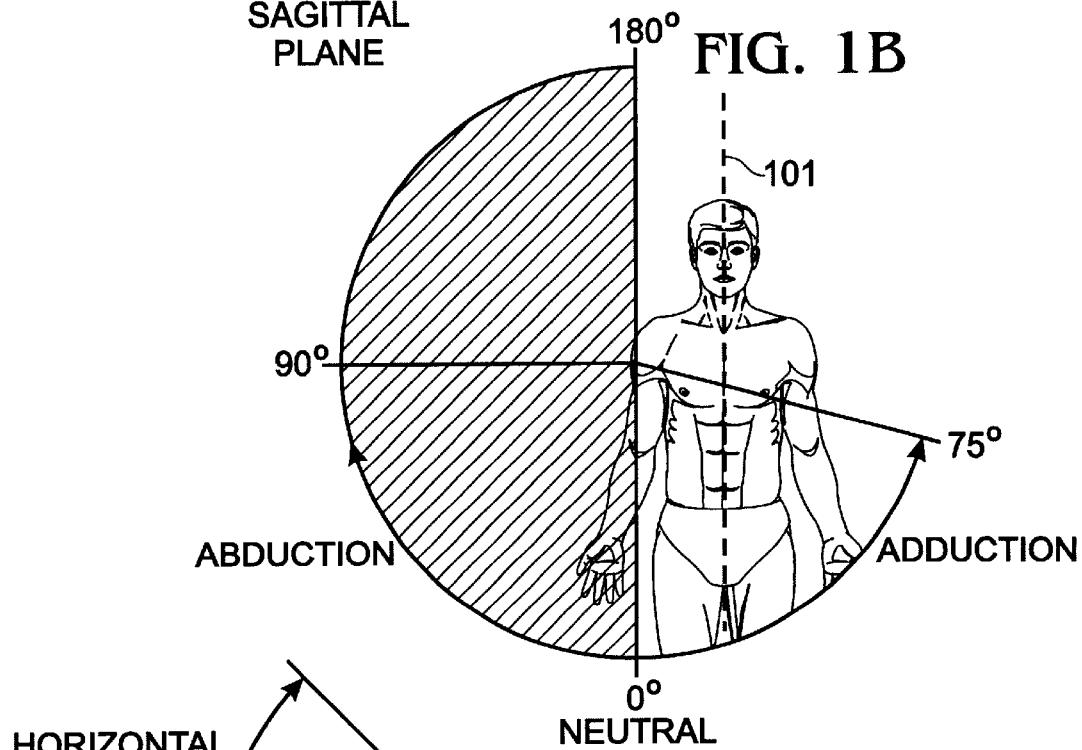
FIG. 1B
FIG. 1D

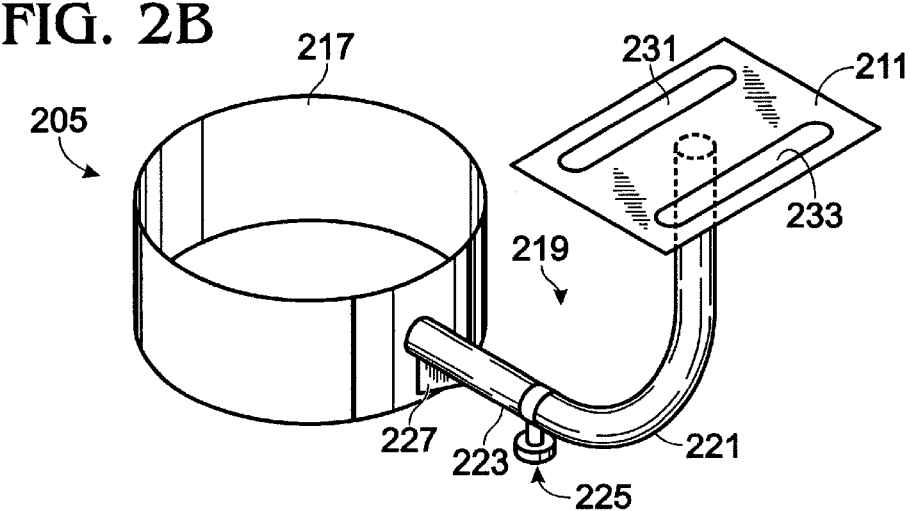
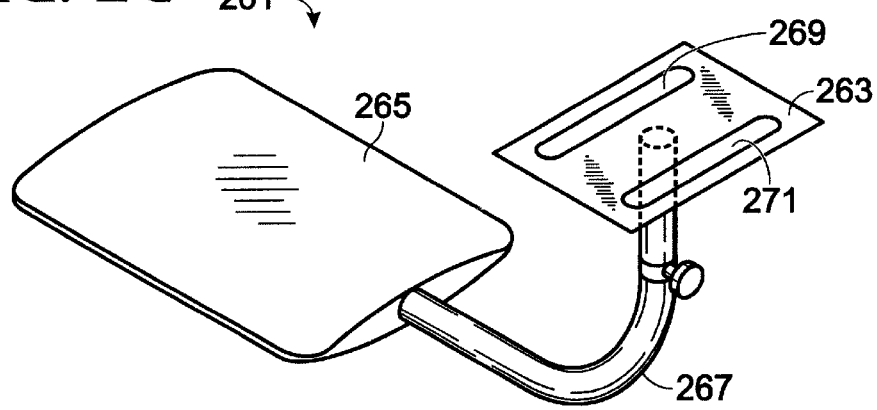
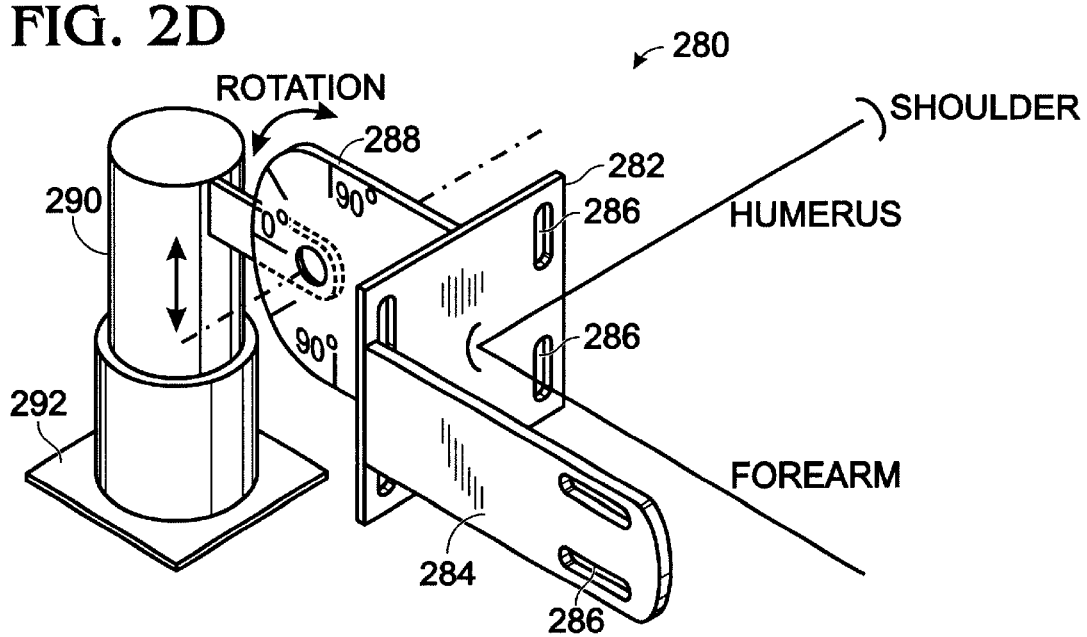

FORCE (FROM LOAD CELL)

RELATIVE DISPLACEMENT

FIG. 8A
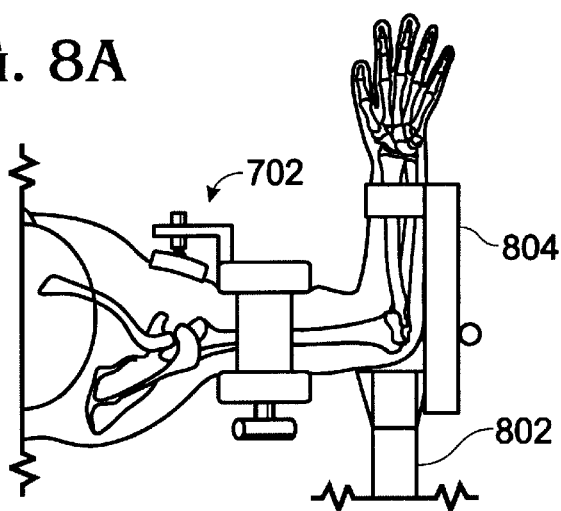
FIG. 8B
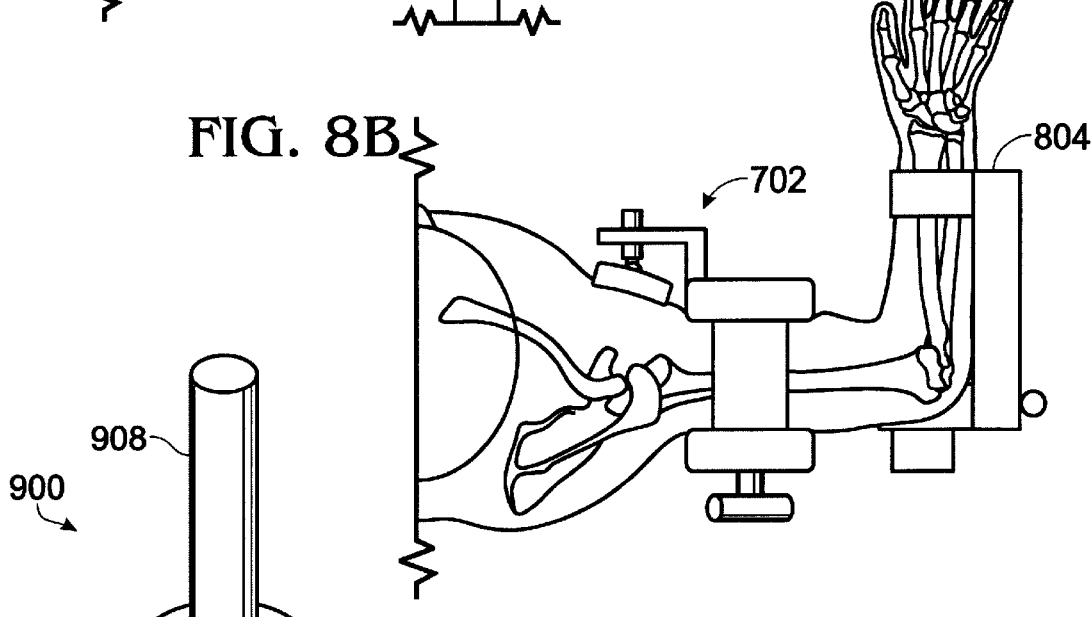
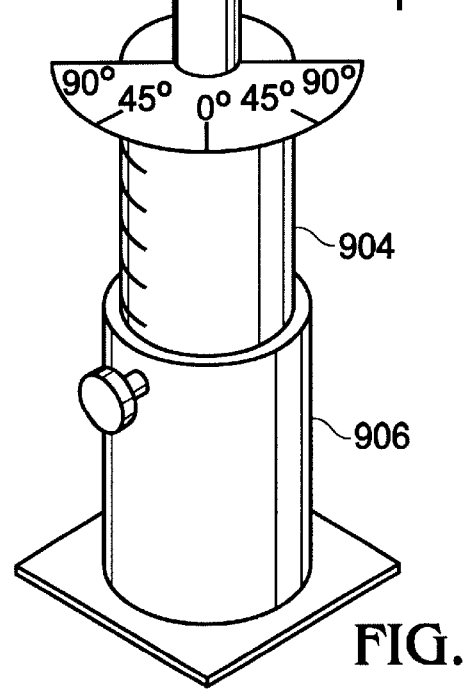
FIG. 9

METHODS AND APPARATUS FOR JOINT LAXITY MEASUREMENTS

FIELD OF THE INVENTION

The invention pertains to methods and apparatus for measurement of joint laxity and stiffness.

BACKGROUND

The evaluation of joint function is important in the assessment, diagnosis, and treatment of injuries and diseases that affect joint function. Typical methods of evaluation rely on a displacement of a limb by a clinician or physician who applies a force to produce the displacement. The usefulness of such methods of evaluation is limited because of the subjective nature of both the force and the displacement measurements, and meaningful comparisons of measurements by different clinicians/physicians or of measurements before and after therapy are not possible. As a result, such measurements are generally not well-suited for the evaluation of the effectiveness of any particular therapy or surgery, nor can such measurements serve as reliable indicators of the extent of joint degeneration or injury.

Other methods of assessing joint function involve static imaging of the joint with X-rays or other imaging techniques. Unfortunately, static imaging does not permit accurate assessment of actual joint function. Accordingly, improved methods and apparatus of assessing joint function are needed.

SUMMARY OF THE INVENTION

According to a first aspect of the invention, instrumented arthrometer systems are provided that numerically measure, record, and graphically display laxity of a body joint, for example, the shoulder (glenohumeral) joint. The arthrometer systems can measure, record, and display stiffness as well. Such instrumented arthrometer systems provide simple, inexpensive joint assessment. As used herein, joint laxity refers to a functional relationship between torque or force applied to a joint and the resulting translational or rotational displacement. Measurement or assessment of joint laxity includes measurement of displacement, force, or both force and displacement. To measure joint laxity, a clinician applies a force or torque to a bone, group of bones, or a joint-reference location of a subject, and the force or torque is measured with a load cell, force glove, or torque glove, and transmitted to a data logger such as a general-purpose personal computer, a handheld computer, or a dedicated computer. Joint displacement is measured using one or more translational and/or one or more rotational detectors. Displacement data also is delivered to the data logger and recorded. The recorded force/displacement or torque/displacement data is processed and displayed with a software program that can be stored on a computer-readable medium such as a floppy disk. A liquid crystal panel, a cathode ray tube monitor, or a printer can be provided to display the recorded data.

For simultaneous measurement of translations in three dimensions, three translational detectors can be provided, or one or more translational detectors that detect translations in multiple directions. Multiple rotational detectors can be used to obtain yaw, pitch, and roll simultaneously.

Data recording and display are conveniently performed using a general purpose personal computer and an associated program. Data can be stored in a form suitable for importation into a spreadsheet program or other data analysis or display program. For portable instrumentation, a laptop computer or a handheld computer can be used. A dedicated processor or computer system, or embedded processor also can be used, if desired.

Translations and rotations can be measured with, for example, the spatial tracking systems available from Polhemus Corporation, Colchester, Vt. These systems use electromagnetic position and orientation measurement devices that permit measurements of joint/bone translations and rotations without cable connections to the subject.

In an embodiment, a clinician applies a force/torque to the joint under measurement using a force/torque glove. The clinician wears the force/torque glove and applies the force/torque manually. The applied force/torque is recorded by the data recording system. In such systems, clinical measurements do not require an additional force/torque applicator. The clinician manipulates the subject's joint or limbs directly, but an instrumented force/torque applicator alternatively can be used.

The instrumented arthrometer permits the acquisition of accurate, objective joint laxity data (i.e., quantitative force-displacement data). Such joint laxity measurements are useful especially for assessing subjects who have suffered capsulo-ligamentous disruption, who have undergone ligamentous surgery, or who are under observation for other conditions. The injured joint can be measured readily for comparison with a similar measurement of the contralateral (healthy) limb to identify differences in ligamentous laxity in various translational planes or about various axes of rotation. In this way, the instrumented arthrometer assists the clinician with diagnosis, aiding in assessing the success or failure of reconstructive surgery, while also providing data for developing a rehabilitation program. In addition, the instrumented arthrometer is largely free of operator error, and can provide reliable and prompt input to medical providers, insurance companies, and health-maintenance organizations for assessing the appropriateness and effectiveness of recommended courses of treatment.

These and other features and advantages of the invention are described below with reference to the accompanying drawings.

BRIEF DESCRIPTION OF THE DRAWINGS

FIG. 2B is a schematic diagram of a joint stabilizer included in the arthrometer of FIG. 2A.

FIGS. 2C–2D are schematic diagrams of respective alternative joint stabilizers.

FIG. 8A is a front view of the arthrometer of FIG. 7A configured for shoulder measurement with a 90 degree abduction and a 0 degree rotation.

FIG. 8B is a top view of the arthrometer of FIG. 7A configured for shoulder measurement with a 90 degree abduction and a 90 degree rotation.

FIG. 9 is a perspective view of an arm support.

DETAILED DESCRIPTION

Embodiments of the invention are described below with respect to laxity measurements performed in vivo on a human shoulder (glenohumeral) joint. These embodiments can be modified to perform measurements on horses or other animals, and need not be performed in vivo.

Figure 1C:
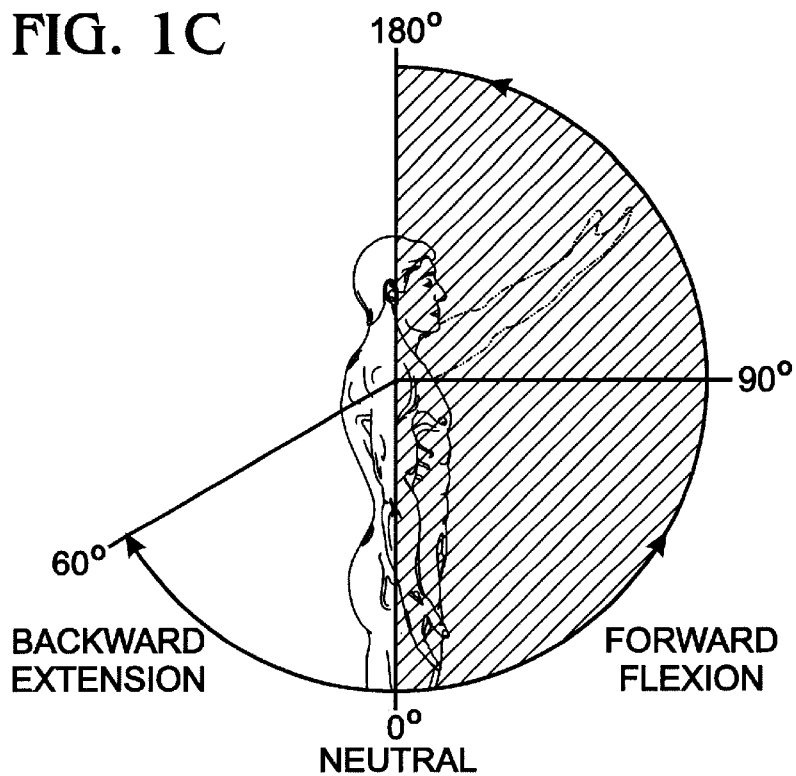
FIG. 1 is a schematic diagram illustrating planes used to describe rotations of a humerus with respect to a shoulder joint.

Definitions useful for describing shoulder motion are provided for convenience. With reference to FIG. 1A, a sagittal plane 101 defines left and right bilateral portions 103, 105, respectively. A coronal plane 107 is orthogonal to the sagittal plane 101. An anterior direction or displacement is a direction or displacement toward the body front. With reference to FIG. 1B, an abduction is an angular displacement in a vertical plane away from the sagittal plane 101 and an adduction is an angular displacement in a vertical plane toward the sagittal plane 101. Referring to FIG. 1C, an anterior angular displacement and a posterior angular displacement in a vertical plane are referred to as a forward flexion and a backward extension, respectively. Referring to FIG. 1D, an anterior angular displacement and a posterior angular displacement in a horizontal plane are referred to as a horizontal flexion and a horizontal extension, respectively.

As used herein, joint laxity is the functional relationship between torque or force applied to a joint and the resulting translational or rotational displacement.

Joint stiffness refers to a force (or torque) required to produce a selected displacement.

Figure 2A:
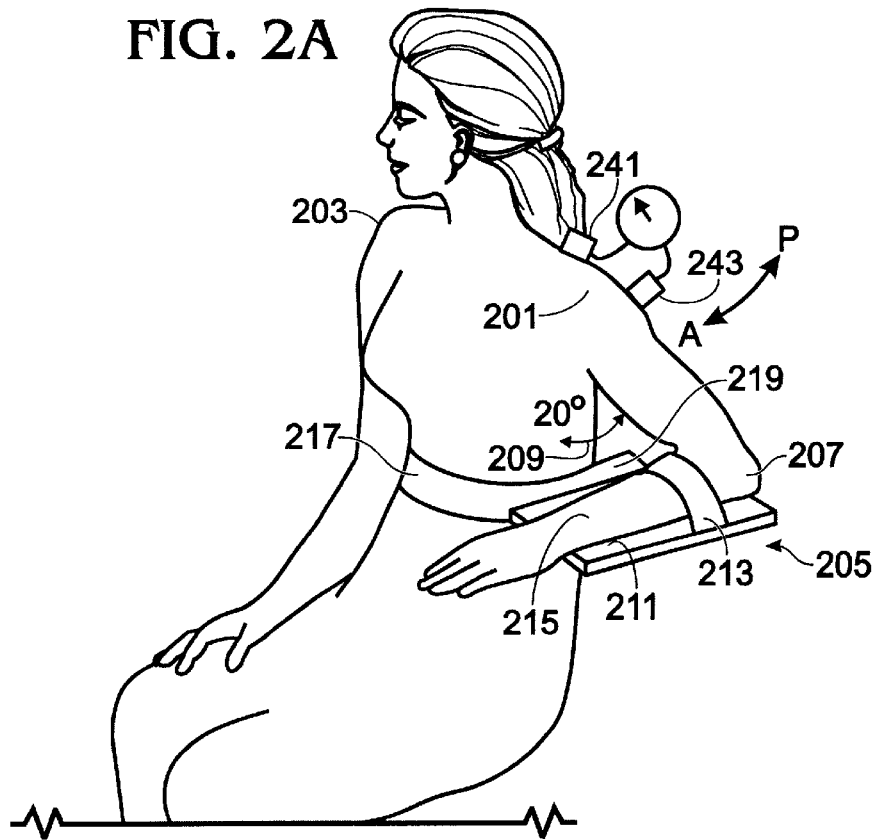
FIG. 2A is a schematic diagram of an instrumented arthrometer configured for measurement of shoulder laxity.

With reference to FIG. 2A, a representative embodiment of an instrumented arthrometer according to the invention is shown configured to assess laxity of a left shoulder joint 201 of a patient 203. The arthrometer includes a joint stabilizer 205 that supports a left elbow 207 at a selected abduction 209. The joint stabilizer 205 includes a forearm rest 211 and a strap 213 for securing a forearm 215 to the forearm rest 211. The forearm rest 211 is attached to an abdominal band 217 by an adjustable connection 219 that permits adjustment of the abduction 209. The abdominal band 217 and the strap 213 use VELCRO or other adjustable fastener for attachment to the patient 203. The joint stabilizer 205 inhibits translational motion of the elbow but permits normal hinging of the elbow.

With reference to FIG. 2B, the adjustable connection 219 includes a sleeve 221 and a shaft 223 that is insertable into the sleeve 223. A set screw 225 is adjustable to fix an insertion of the shaft 221 into the sleeve 223. The joint stabilizer 205 also can include an additional adjustment mechanism 227 for attachment of the sleeve 223 to the abdominal band 217. In addition, the forearm rest 211 can be curved, and can include slots 231, 233 for insertion of the strap 213.

Referring further to FIG. 2A, the arthrometer includes displacement sensors 241, 243 attached to the patient at joint-reference locations corresponding to an acromion process and a humeral head, respectively, at the shoulder 201. The displacement sensors 241, 243 are configured to measure displacements in an anterior (A) or posterior (P) direction. For measurements of joint laxity of other joints or of other glenohumeral displacements, different joint-reference locations can be specified. The displacement sensors 241, 243 can be dial indicators, electronic calipers, or other mechanical or electronic displacement sensors, and can be analog or digital. Battery-powered displacement sensors are particularly convenient. The displacement sensors 241, 243 record maximum displacements and are resettable after completion of a measurement. As shown in FIG. 2A, the patient 203 is in a seated position for comfort, but other positions are satisfactory.

With the arthrometer of FIGS. 2A–2B, an anterior-posterior drawer test is performed by fixing the displacement sensors 241, 243 with respect to the acromion and the humeral head, respectively, and establishing the abduction 209 with the joint stabilizer 205. Typically, the abduction 209 is adjusted to be within a range of about 0 to about 90 degrees before performing the anterior-posterior drawer test, and the patient 203 is seated during the test. The acromion is stabilized, and an anterior force (load) is applied to the humerus. A displacement produced by the applied force is determined based on displacements indicated by the displacement sensors 241, 243. Typically, a clinician stabilizes the acromion with one hand and applies a force to the humerus with the other hand. The anterior displacements are recorded manually or, alternatively, a general-purpose computer or a dedicated controller can be provided that automatically logs displacement data. After completion of the measurement, the clinician resets the displacement sensors 241, 243 before measuring and recording the posterior displacement obtained by applying a posterior load, or prior to repeating the anterior-displacement measurement. Laxity tests performed with anterior or posterior forces are referred to as anterior drawer and posterior drawer tests, respectively.

Upon obtaining anterior/posterior patient data, the clinician or a treating physician can compare the measured displacements to respective normal ranges of displacements. Alternatively, the displacements can be compared with similar measurements performed before therapy (such as physical therapy, surgery, or medication, or other treatment) to determine the effectiveness of the therapy. In addition, a comparison of displacements for a right shoulder and a left shoulder can be used to assess joint function. Such bilateral comparisons permit, for example, an uninjured or healthy joint of the patient to serve as a reference for assessing any loss of function in an injured or diseased joint. Because the displacements are quantitively recorded, comparisons of displacement data tend to provide reliable joint assessment, without being limited by clinician subjectivity.

The arthrometer of FIGS. 2A–2B includes two displacement sensors 241, 243. However, if the acromion process can be fixed adequately so that any displacement of the acromion process can be neglected, a single displacement sensor can be used.

FIG. 2C is a perspective view of an alternative joint stabilizer 261 that illustrates a forearm tray 263 attached to a seat 265 by an abduction adjustment 267. Slots 269, 271 are provided for insertion of a strap (not shown) that secures the forearm to the forearm tray 263. The joint stabilizer 261 is convenient for laxity measurements of a seated patient because the patient's weight serves to support the forearm tray 263, avoiding the inconvenience or embarrassment associated with application of the abdominal band 217.

An alternative joint stabilizer 280 is illustrated in FIG. 2D. Mounting plates 282, 284 for the humerus and forearm, respectively, are provided with slots 286 for insertion of straps (not shown) that secure the humerus and forearm to the respective mounting plates 282, 284. A rotatable mount 288 permits the mounting plates to be rotated about an arbitrary axis to set an adduction or other angle. The rotatable mount 288 is attached to a column 290 that is extendable to adjust a height of the mounting plates 282, 284. The column 290 is supported by a base 292 that is secured to, for example, a floor-mounted support or a chair that supports the patient.

Figure 2E:
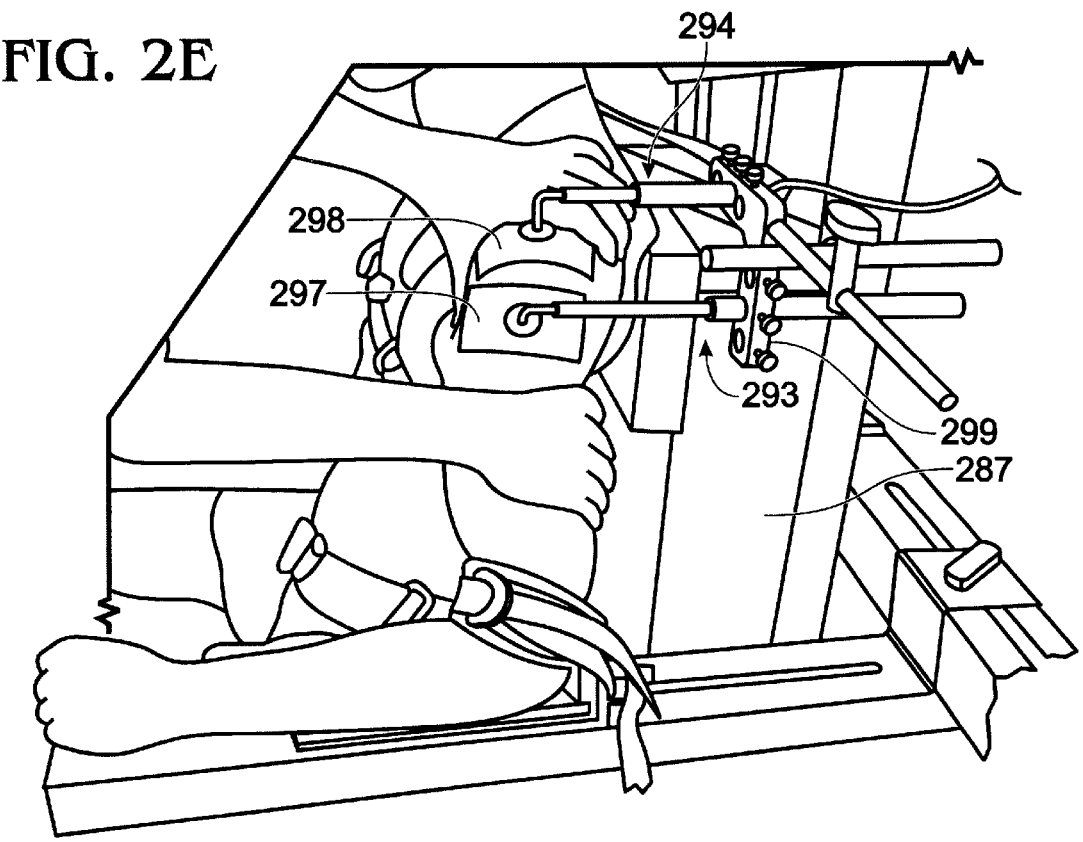
FIG. 2E is a partial schematic diagram illustrating displacement sensors positioned at joint-reference locations on a glenohumeral joint.

A specific arrangement of displacement sensors 293, 294 is illustrated in FIG. 2E. The displacement sensors 293, 294 include respective extensions 295, 296 that extend to contact respective joint-reference locations 297, 298. A mounting bracket 299 secures the displacement sensors 293, 294 to a post 287 that, for convenience, attaches to a chair in which the patient is seated.

Figure 3A:
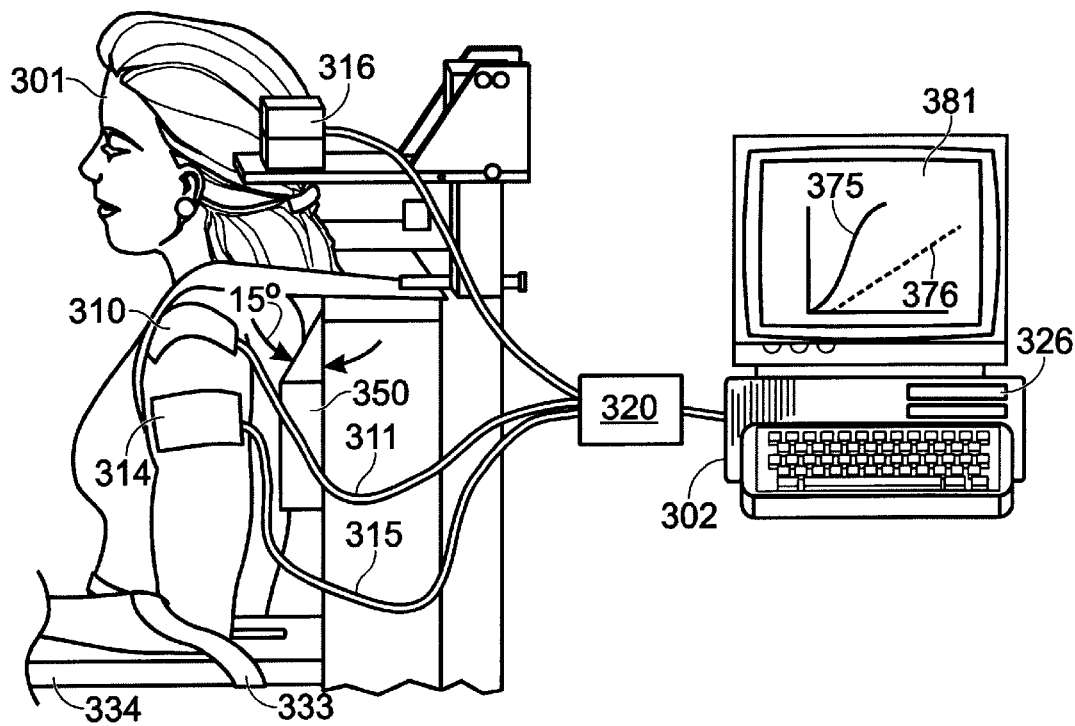
FIGS. 3A–3B are illustrations of an instrumented arthrometer that includes electromagnetic displacement sensors and that is configured for anterior/posterior and inferior/superior displacement measurements of a glenohumeral joint.

With reference to FIG. 3A, an instrumented arthrometer configured for glenohumeral joint-laxity measurements of a patient 301 includes a controller 302 such as a general purpose computer using a MICROSOFT WINDOWS operating system or other computer. Electromagnetic position sensors 310, 314 are provided for attachment to the patient 301 at locations corresponding to the acromion process and humeral head at the shoulder being measured. A field transmitter 316 establishes a magnetic field, and position/displacement data transmitted is based on respective displacements of the electromagnetic position sensors 310, 314 relative to the magnetic field. A position-data processor 320 in communication with the electromagnetic position sensors 310, 314 receives the transmitted position data and provides respective displacement data based on the transmitted position data. The data processor 320 can be implemented in hardware, software, or a combination of hardware and software, and can be provided in the controller 302 or as a separate module. In the embodiment shown in FIG. 3A, the data processor 320 is external to the controller 302. While the position sensors 310, 314 connect to the position-data processor 320 with respective cables 311, 315, the position sensors 310, 314 can be provided with wireless transmitters so that cables are unnecessary.

Sensors suitable for the electromagnetic position sensors 310, 314 are available from, for example, Ascension Technology Corporation, Burlington, Vt, and Polhemus Corporation, Colchester, Vt. A position-sensing system based on such sensors is described in Reis, U.S. Pat. No. 5,961,474, which incorporated herein by reference. Other suitable position sensors and threedimensional position trackers can be used based on electromagnetic, optical, acoustic, or inertial position sensing. If the electromagnetic positions sensors 310, 314 provide displacement data for more than one direction, or rotational data for one or more axes of rotation, then such data can be recorded during laxity testing as well. For example, if a clinician produces an inferior displacement during an intended measurement of an anterior displacement, the inferior displacement can be noted or recorded.

The arthrometer of FIG. 3A is configured to perform anterior-posterior drawer measurements in a manner similar to that used with the arthrometer of FIG. 2A. Glenohumeral laxity is measured by stabilizing the elbow against an arm rest 334 with a strap 333 while the subject is seated in an immobilization chair. A wedge 350 supports a shoulder area. While the subject is seated with the elbow stabilized, the clinician stabilizes the shoulder with one hand and applies a force with the other hand. For anterior-posterior displacement measurements, a joint stabilizer such as those shown in FIGS. 2B–2D can be used. Displacement data is generated by the controller 302 or the data processor 320, and typically can be automatically recorded and stored on a hard disk, a floppy disk, or transmitted to a network for storage or further transmission.

Although the arthrometer of FIG. 3A is shown configured for measurement of glenohumeral joint function, the arthrometer is also applicable to measurements of other joints, including knees, elbows, ankles, and other joints. With reference to FIG. 3A, application to a selected joint (e.g., a knee or ankle) is facilitated by a joint-configuration software module 326 responsive to joint selection by the clinician. The software module 326 includes computer-executable instructions for displaying instructions concerning joint-specific measurement procedures and sensor placements. In addition, the software module 326 directs comparisons of measured displacement data to stored reference displacement data for the selected joint so that, for example, measured displacement data for a knee is compared to knee-specific displacement norms. Measured data and reference data are conveniently displayed on a display screen 381 as corresponding graphs 375, 376, respectively. For measurements of joints other than the shoulder, an elbow stabilization is generally unnecessary. A joint stabilizer can be reconfigured as needed, or an alternative joint-specific stabilizer can be provided.

Figure 3B:
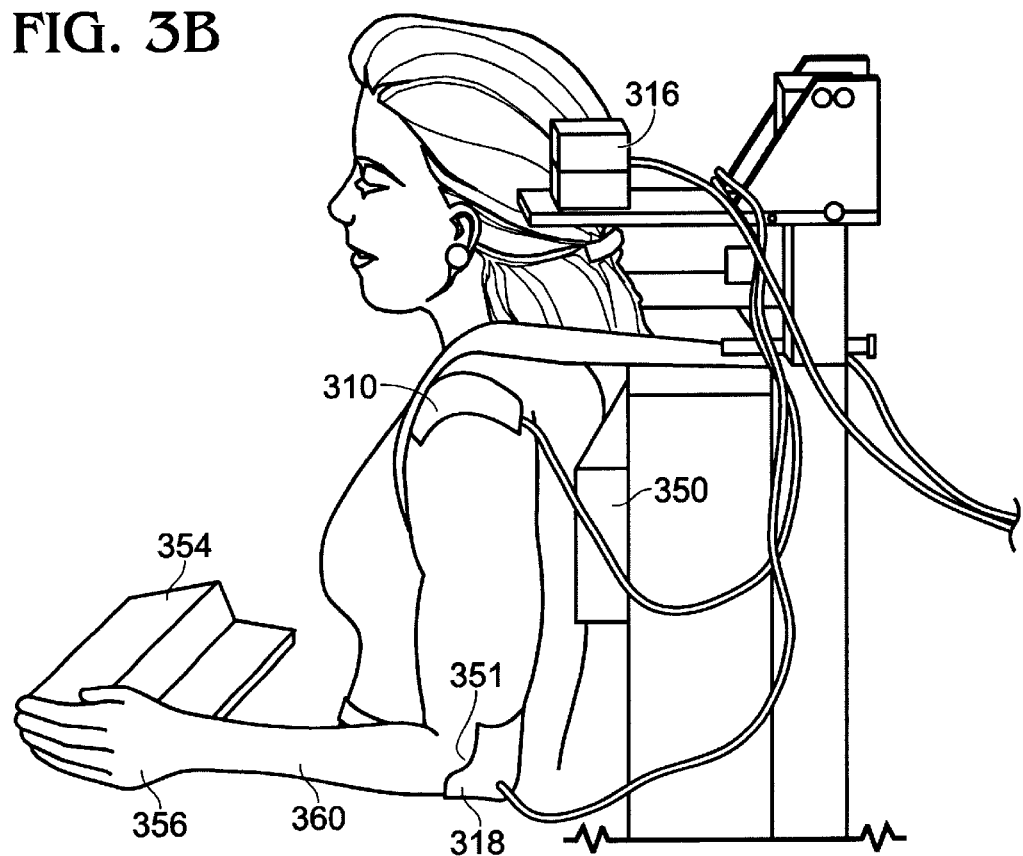

The arthrometer shown in FIG. 3A is configured for measurement of shoulder joint anterior-posterior displacements. With reference to FIG. 3B, the arthrometer can be configured to measure inferior-superior displacements by situating an electromagnetic sensor 318 near the elbow 350, without using a joint stabilizer. The clinician then applies an inferiorly/superiorly directed force to the humerus at a region 360 while stabilizing the acromion process, allowing a hand 356 to rest on a tray 354, and recording force data and corresponding displacement data from the sensors 310, 318. An additional sensor such as the sensor 318 is not necessary if the sensor 306 can be moved.

Figure 4:
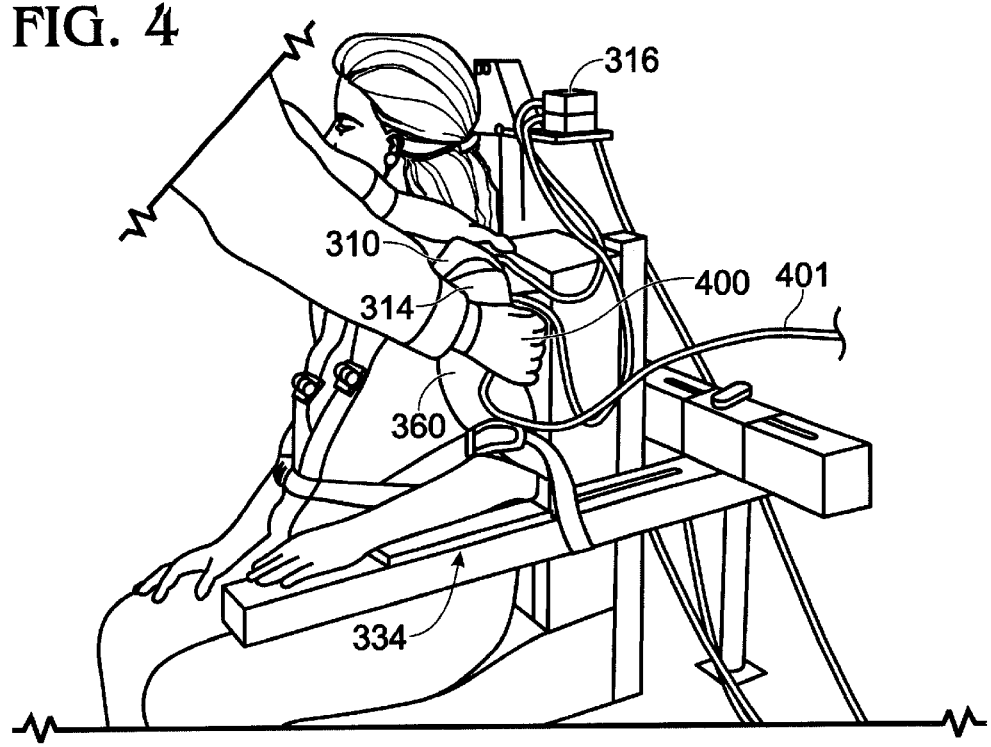
FIG. 4 is a diagram of an instrumented arthrometer that includes a force glove.

The arthrometers of FIG. 2A and FIGS. 3A–3B provide joint-displacement data produced by manual application of a force or torque by a clinician, without quantification of the applied force or torque. With reference to FIG. 4, an instrumented arthrometer similar to the arthrometer of FIGS. 3A–3B includes a force-sensing glove 400 worn by the clinician as force or torque is applied. The glove 400 is in communication with the controller 302 with a cable 401. Force gloves are commercially available from, e.g., Virtual Technologies, Inc., Palo Alto, Calif., and are described in, for example, Kramer et al., U.S. Pat. No. 6,042,555, which is incorporated herein by reference. The clinician applies a force manually and the magnitude and direction of the applied force are sensed by the force-sensing glove 400, and force data are supplied to the controller 302. Anterior-posterior or inferior-superior displacement measurements are performed as described above, and force or torque data and corresponding displacement data are communicated to the controller 302. Therefore, displacement as a function of applied force is recorded with force data quantified by the force glove 400, without reliance on a clinician's estimate of applied force. The controller 302 can be configured to establish a range of forces to be applied, or a maximum force to be applied, and provide an audible or other indication that the range has been fully recorded or that a maximum force has been reached. Such force ranges and maximum forces can be based on prior data or physician instructions for a specific patient, and can be joint-specific.

With quantitative force and displacement data, subjectiveness in joint assessment is largely eliminated, and reliable bilateral joint comparisons of joints (e.g., left shoulder-right shoulder comparisons) and pre- and post-treatment comparisons can be made. Such comparisons not only aid in assessment and treatment, but also can serve to determine patient treatment requirements objectively in order to obtain treatment authorization from a health insurance plan.

Figure 5:
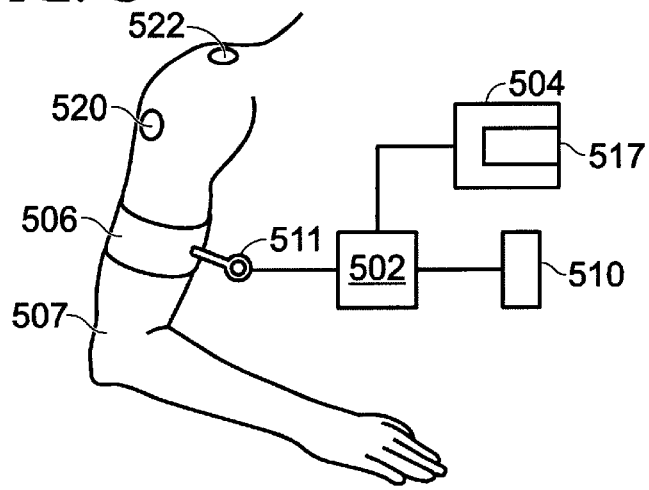
FIG. 5 is a partial schematic diagram of an instrumented arthrometer that includes a force sensor including a load cell.

While the force glove 400 is especially convenient for use in an instrumented arthrometer system, other force sensors alternatively can be used. With reference to FIG. 5, a force sensor includes a load cell 502 in communication with a controller 504. The load cell 502 is connected to an arm cuff 506, typically an inflatable air cuff, that surrounds an arm of a patient. The arm cuff 506 can be secured with a VELCRO strap or other attachment. The force sensor also includes a handle 510 and is removably secured to the air cuff 506 with an eye bolt 511. Force is applied by the clinician by pulling the handle in a selected direction while the load cell 502 communicates the applied force to the controller 504. The air cuff 506 is similar to a standard air cuff used in blood-pressure measurements. As an alternative to the air cuff, an arm band of VELCRO can be secured about the humerus, and a web loop provided on the arm band for attachment of the load cell. The web loop also can be used with the arm cuff, instead of the eye bolt. The clinician can rotate the air cuff 506 (or the arm band) to apply a force to the humerus and the glenohumeral joint through the load cell 502 in either the anterior or posterior direction. For convenience, the air cuff 506 can be provided with two web loops or two eye bolts (not shown), so that anterior and posterior measurements can be made without moving or adjusting the air cuff. The controller 504 includes an analog-to-digital converter 517 that produces a digital representation of the applied force. As shown in FIG. 5, the displacement sensors 520, 522 are attached near the acromion process and humeral head, respectively, for measurement of anterior or posterior displacements.

The instrumented arthrometers described above permit detailed study of ligamentous laxity under various conditions. Forces of 180 N or less are generally applied to a glenohumeral joint, so that load cells having a measurement range of up to 180 N are adequate. Athletic individuals may require forces larger than 180 N.

Figure 6A:
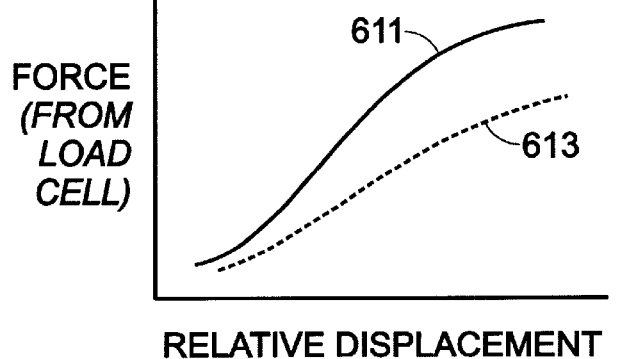
FIGS. 6A–6B are representative graphs of joint laxity data.
Figure 6B:
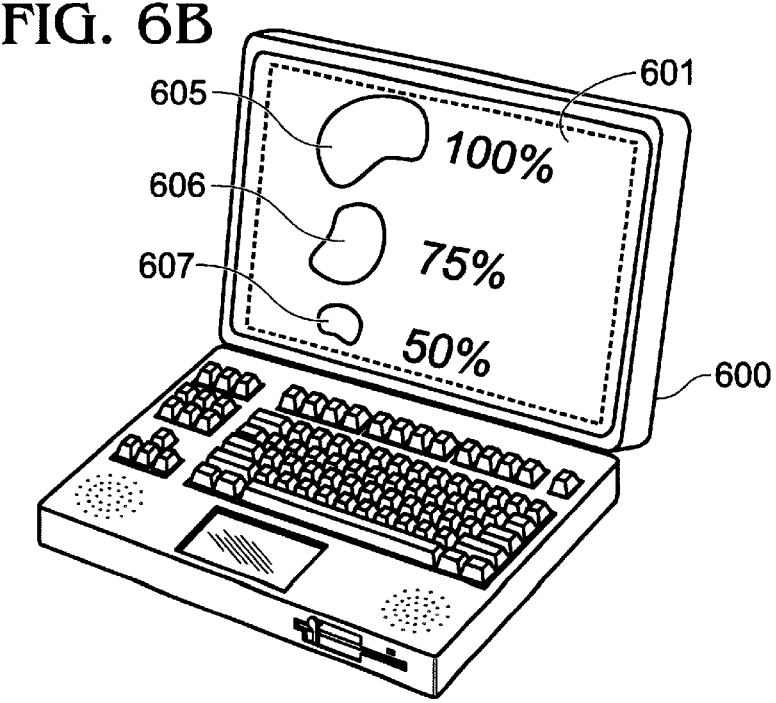
Figure 7A:
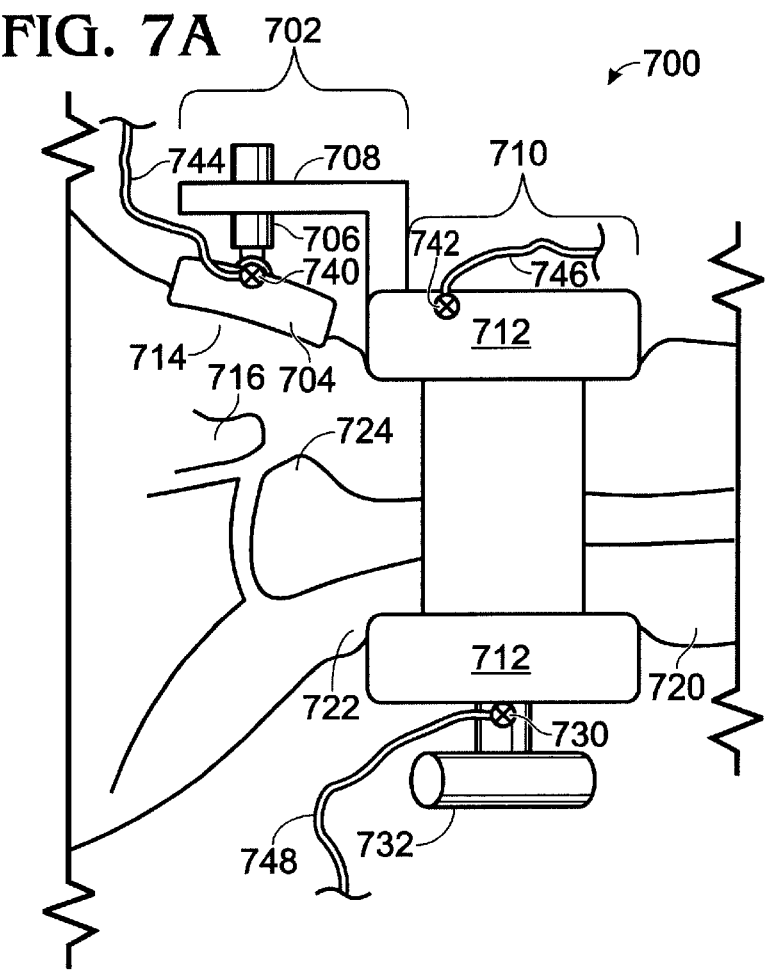
FIG. 7A is a sectional view of a self-contained, subject-mountable arthrometer fixed to a subject.
Figure 7B:
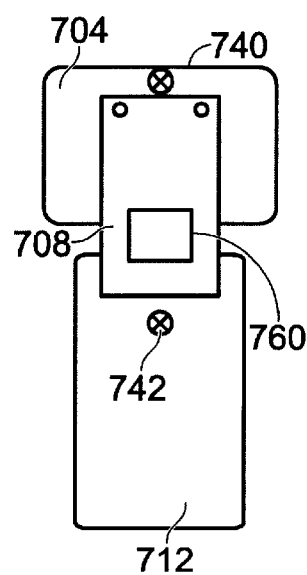
FIG. 7B is a plan view of the arthrometer of FIG. 7A.
Figure 7C:
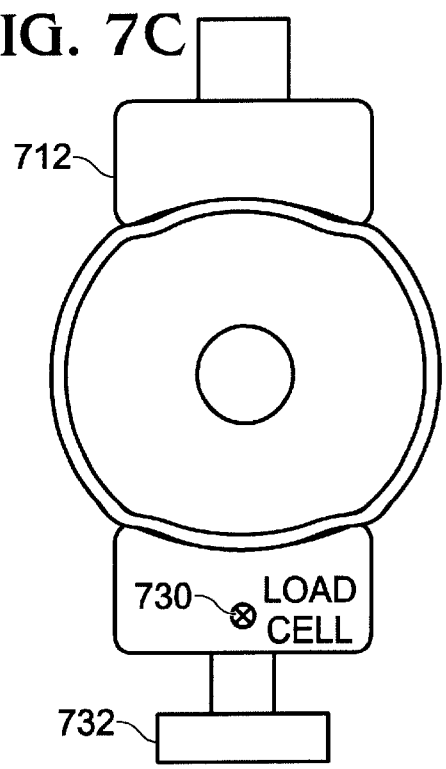
FIG. 7C is a sectional view of a displacement position assembly of the arthrometer of FIG. 7A.
Figure 7D:
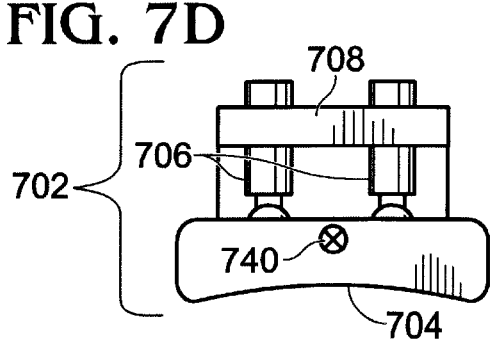
FIG. 7D is a sectional view of reference position assembly of the arthrometer of FIG. 7A.

Glenohumeral laxity data typically is displayed on a computer display with force as a function of displacement. Example plots of force and displacement are shown in FIGS. 6A–6B. With reference to FIG. 6A, a curve 611 of measured force as a function of measured displacement is displayed. Also displayed is a curve 613 of reference data. Referring to FIG. 6B, glenohumeral laxity data can be recorded, displayed and plotted as three-dimensional surface plots 605, 606, 607 on a display 601 of a computer 600. The three-dimensional surface plots 605, 606, 607 show laxity of the joint as a function of different loads and directions. For example, if the clinician applies a force having a constant magnitude of 90 N but varies the direction in which the force is applied, the displacement can be graphed as the three dimensional surface plot 607 that shows displacements in the anterior, posterior, and inferior directions as well as combinations of these directions. Such a graph permits the clinician to determine the directions in which larger or smaller displacements are obtained for a constant force. If another force having a larger constant magnitude is applied, for example, 135 N the surface plot 606 is obtained. This surface plot generally corresponds to larger displacements. FIG. 6B also shows the surface plot 605 corresponding to a force of about 180 N.

FIGS. 7A–7D contain various views of a self-contained, subject-mountable arthrometer 700. The arthrometer 700 includes a reference position assembly 702 having a pad 704 that is mounted to rods 706 that are slidable within bores of an adjustment base 708. The pad 704 is generally adjusted to contact a reference location 714, shown in FIG. 7A as a location near an acromion process 716. A displacement position assembly 710 fixed to an upper arm 720 includes pads 712 configured to contact a reference location 722, shown in FIG. 7A as a location near a humeral head 724. The pads 712 are fixed to the upper arm 720 with straps such as VELCRO straps. A load cell 730 attaches to the pad 704 and to a handle 732.

Displacement sensors 740, 742 attach to the reference position assembly 702 and the displacement position assembly 710. The displacements sensors communicate displacements via respective cables 744, 746 and force data is communicated from the load cell 730 via a cable 748. While the arthrometer 702 is configurable to communicate force/displacement data to an external computer or data logger, a data display 760 can be provided that mounts to the arthrometer 702. Alternatively, displacement sensors can be provided that indicate displacements directly on the arthrometer 702 without communication to or from an external computer or data logger.

FIG. 8A illustrates the arthrometer 702 mounted to a subject for a shoulder laxity measurement with a 90 degree abduction and a 0 degree rotation and for anterior/posterior applied forces. A humerus support 802 and a rotational control arm 804 provided for setting and adjusting the rotation and abduction. FIG. 8B illustrates the arthrometer 702 configured for measurement with a 90 degree abduction and a 90 degree rotation.

FIG. 9 is a perspective view of an arm support 900 that includes a post 904 that is adjustable in a base 906. A rotational arm 908 is mounted to the post 904. The arm support 900 is configurable to adjust various shoulder angles.

The methods and apparatus described above can be configured for portability. For example, a handheld computer, displacement sensors, and a force sensor can be incorporated into a briefcase-sized instrument that can include a printer, disk drives, and a network connection. Instruments can also be configured for operating room operation. Because force/displacement data is provided nearly simultaneously with the application of force to a joint, a physician can use this data during surgery.

As described above, methods and apparatus are applied to a static or quasistatic assessment of joint laxity. Typically, force (F) and displacement (D) are related as $F=kD$ plus higher order terms in D (e.g., terms proportional to $k_2 D^2$), wherein k is a joint force constant. In some applications, joint assessment can be based on measurement, display, or recording of the joint force constant k. In addition, for a moving joint, the force-displacement relationship includes terms based on velocity v, i.e., $F=kD+cv$, wherein c is a viscoelastic constant. Measurements of forces that include viscoelastic contributions can be performed with the methods and apparatus described above.

While the invention is described above with reference to several examples, it will be appreciated by those skilled in the art that these embodiments can be modified in arrangement and detail without departing from the scope of the invention.

What is claimed is:

1. A method for assessing joint function, comprising:
   displacing a limb associated with a joint;
   measuring a displacement produced by the limb displacement;
   determining a force associated with the limb displacement; and
   comparing the measured force and the measured displacement with a reference force and a reference displacement, respectively.

2. The method of claim 1, further comprising providing the reference force and the reference displacement based on measurements of a corresponding bilaterally symmetric joint.

3. The method of claim 1, further comprising providing the reference force and the reference displacement based on measurements obtained from a reference population.

4. The method of claim 1, further comprising providing the reference force and the reference displacement based on measurements of the joint prior to a treatment.

5. A method of approving a subject for treatment, comprising:
   quantitatively measuring laxity of a joint of the subject;
   comparing the measured laxity to a reference laxity; and
   approving the subject based on the comparison.

6. An arthrometer, comprising:
   at least one displacement sensor;
   a force sensor situated and configured to measure a force;
   a limit indicator configured to indicate that the measured force is within a predetermined force range;
   a controller that receives a displacement of the joint from the displacement sensor, the displacement corresponding to the force measured by the force sensor;
   a computer-readable medium containing a reference displacement and a reference force; and
   a display configured to display the displacement of the joint, the force measured, the reference displacement, and the reference force.

7. An apparatus for measuring joint laxity, comprising:
   first and second displacement sensors that provide first and second displacement measurements, respectively, the first and second displacement sensors being configured to be attachable to corresponding first and second joint-reference locations;
   a force sensor that includes a force glove and configured to provide a force measurement; and
   a controller that receives the force measurement and the displacement measurements.

* * * * *